United States Patent [19]

Middleton et al.

[11] Patent Number: 4,798,607

[45] Date of Patent: Jan. 17, 1989

[54] PROCESS OF CROSSLINKING A POLYURETHANE PROSTHESIS WITH A HALOALKYLISOCYANTE

[76] Inventors: Ian P. Middleton, 15, Timway Drive, West Derby, Liverpool, United Kingdom, L12, 4YR; Jerzy Paprotny, ul. Mewy 5/41, 44-100 Gliwice, Poland

[21] Appl. No.: 61,758

[22] Filed: Jun. 15, 1987

[30] Foreign Application Priority Data

Jul. 4, 1986 [GB] United Kingdom ............... 8616416

[51] Int. Cl.$^4$ ............................................... A61F 2/06
[52] U.S. Cl. .......................................... 623/1; 623/11; 623/66; 525/457; 264/22; 264/48; 264/83; 264/DIG. 42; 264/DIG. 77
[58] Field of Search .................. 623/1, 2, 11, 12, 13, 623/66; 427/2; 525/457; 264/22, 24, 48, 83, 232, 340, DIG. 41, DIG. 42, DIG. 77

[56] References Cited

U.S. PATENT DOCUMENTS

| | | | |
|---|---|---|---|
| 2,929,800 | 3/1960 | Hill | 528/64 |
| 3,442,843 | 5/1969 | Keberle et al. | 525/457 |
| 3,545,911 | 12/1970 | Papero, Jr. et al. | 264/83 |
| 4,016,303 | 4/1977 | Poirier et al. | 427/2 |
| 4,044,404 | 8/1977 | Martin et al. | 623/1 |
| 4,062,834 | 12/1977 | Gilding | 260/77.5 |
| 4,131,114 | 12/1978 | Kirkpatrick et al. | 427/2 |
| 4,281,992 | 8/1981 | Colpitts et al. | 433/202.1 |
| 4,314,948 | 2/1982 | Koenig et al. | 260/453 P |
| 4,381,380 | 4/1983 | LeVeen et al. | 604/265 |
| 4,608,416 | 8/1986 | Schupp et al. | 525/457 |
| 4,623,553 | 11/1986 | Ries et al. | 427/2 |

FOREIGN PATENT DOCUMENTS 0009941 4/1980 United Kingdom .
2120946 12/1983 United Kingdom .

OTHER PUBLICATIONS

Pure and Applied Chemistry 52, (1980), pp. 1851-1855.

*Primary Examiner*—Richard J. Apley
*Assistant Examiner*—Paul Prebilic
*Attorney, Agent, or Firm*—Robert L. Minier

[57] ABSTRACT

A process is disclosed for producing a medical prosthesis by forming the prosthesis from an uncrosslinked polyurethane and then at least partially crosslinking the polyurethane with a vaporizable halo alkylisocyanate. The haloalkylisocyanate (e.g. chloromethylisocyanate) is reacted with the uncrosslinked polyurethane at a temperature which will not degrade or soften the polyurethane, (in its uncrosslinked form) in order to crosslink the polyurethane.

12 Claims, No Drawings

PROCESS OF CROSSLINKING A POLYURETHANE PROSTHESIS WITH A HALOALKYLISOCYANTE

The present invention describes a facile cross-linking process for a number of polyurethanes with particular emphasis on those used for biomedical applications. In particular, the present invention relates to electrostatically spun products, such as tubular vascular grafts, and to methods for their manufacture.

The techniques of electrostatic spinning containing or comprising a fiber forming material is well known and is described, for instance, in U.S. Pat. No. 4,044,404.

This technique has been applied to the production of tubular products such as vascular grafts For instance DE-A-No. 2 704,771.8 describes the preparation of such tubular products by the electrostatic spinning of liquids to give fibers which are collected upon an electrostatically charged former having a configuration corresponding to the desired internal configuration of the tubular product.

A similar process can be used to produce non-tubular products by using an electrostatically charged former of appropriate shape.

An improvement of the process for forming tubular products is described in EP-A-No. 0,009,941 which describes a process in which an auxiliary electrode or set of electrodes is used to vary the orientation of the fibers so as to alter the balance between the longitudinal strength and the bursting strength of the tubular product.

Other methods for imparting some directional bias to the fibers in a tubular product include the use of variations in the speed of mandrel rotation as described in GB-A-No. 2,120,946 and GB-A-No. 2,121,286.

Further improvements in the production of tubular products by electrostatic spinning are described in out copending British patent application No. 8524541 filed on Oct. 4th, 1985, which describes a tubular fibrous structure comprising small diameter fibers and substantially larger diameter fibers, said smaller diameter fibers being randomly oriented in the fibrous structure, said larger diameter fibers being embedded in a matrix of said small diameter fibers and said larger diameter fibers being generally oriented circumferentially with respect to the longitudinal axis of said tubular structure.

Such tubular products may be used, for instance, as artificial urinary or bile ducts, artificial heart components, artificial trachea, components of auxiliary medical equipment which come into lengthy contact with living tissue or, preferably, artificial vascular grafts.

Electrostatically spun non-tubular products also find use in the medical filed, for instance as reinforcements for weakened tissue areas.

The electrostatically spun products for medical use may be made of any biocompatible, non-absorbable or absorbable fiberizable material. A "fiberizable" material is one which is capable of forming a solution or melt which can be electrostatically spun to form fibers. Suitable fiberizable materials include polyesters, such as polyethylene terephthalate, fluorinated compounds, especially fluorinated hydrocarbons such as polytetrafluoroethylene, silicones, polyamides, such as the Nylons, polyacrylonitrile and urea/formaldehyde resins. However, the preferred fiberizable materials are polyurethanes, in particular polyether urethane ureas. Such materials are well known in the art and are available under the trademarks Biomer (from Ethicon) and Mitrathane (from Mitral Medical International, Inc., Colorado).

The polyurethane sold under the trademark Biomer is a polytetramethylene ether polyurethane urea, and a method for preparing it is described in U.S. Pat. No. 4,062,834.

Other poly(ether urethanes) prepared from polytetramethylene glycol such as Pellethane (Bayer) and Tecoflex (Thermedic) may be fabricated in tubular form by processes such as extrusion and dip casting for use as catheters, pacemaker leads and applications cited earlier for electrostatically spun products. A review of the use of polyurethanes as surgical implants is given by Boretos, J. W., in Pure and Applied Chemistry, 52, 1851, 1980.

The known electrostatically spun products for medical use are of necessity porous. This is an advantage in that it facilitates formation of scar tissue through the pores. Thus, the product can be anchored in living tissue not only by any sutures placed through the product but also, and more effectively, by the regenerated natural tissue.

The known electrostatically spun properties after manufacture have very good physical properties for medical use, and these properties can be to a certain extent improved by the method of manufacture of the product, as shown in the patent specifications referred to above. These products are also, in generally, adequately flexible for their intended use.

However, once in place in the body, the products are subject to various stresses. For instance, an artificial vascular graft will be subject to radial stress, due to the pumping of the blood through the graft, axial stress, due to stretching of the graft, and flexural stress, due to bending of the part of the body containing the graft. Under such stress, there will be a tendency for the polymeric material from which the product is made to creep, with a concomitant loss of shape and physical properties.

The tendency to creep could be reduced by increasing the thickness of the product. However, this would be disadvantageous because it would decrease the porosity and flexibility of the product and make it more difficult for the surgeon to handle it during a surgical procedure.

It would therefore be desirable to produce an electrostatically spun product which retained its porosity, flexibility and physical properties, but which was not subject to creep following long term use.

Problems associated with the tendency to creep are general and the previous statement applies equally to articles manufactured from polyurethanes by fabrication processes other than electrostatic spinning.

The present invention therefore provides an electrostatically spun product comprising a structure of fibrous polymeric- material wherein the polymeric material in the individual fibers is at least partially cross-linked but in which there, is substantially no cross-linking between the individual fibers.

The present invention also provides a process for producing such an electrostatically spun product which comprises electrostatically spinning a melt or solution of a fiberizable polymeric material onto an appropriately shaped former and exposing the thus formed product to a vapour of a cross-linking agent.

It has been found surprisingly that the use of a vapour-phase cross-linking agent leads to cross-linking of the polymeric material within the fibers but does not lead to any significant degree of cross-linking between the fibers. Thus, the formed product when treated in this way retains substantially its original microscopic and macroscopic appearance and also retains substantially its original flexibility and porosity. However, its physical properties, such as elongation, flexural and burst strengths, and in particular its resistance to creep, are significantly increased.

Moreoever, it has proved impossible to cross-link the polymeric material prior to the electrostatic spinning as this either decreases the solubility of the material or increases its melting point to such an extent that the material can no longer be electrostatically spun.

The product of the present invention may be spun by any of the methods set out above or any variation or development of such methods. Preferably, the method described in our copending British patent application No. 8524541 is used.

The cross-linking agent which is used will depend on the polymeric material used to form the product. The cross-linking agent can be any one of those known in the art as cross-linking agents for the particular polymer used provided that the agent can exist as a vapour at a temperature below that at which the polymeric material in its uncross-linked form begins to degrade or soften. If desired, vacuum may be applied to increase the degree of vapourization of the agent, which may be a liquid or a sublimable solid.

Selection of a suitable cross-linking agent will be merely a matter of routine experiment for a skilled person.

If desired, the product may be held at an elevated temperature in order to enhance the cross-linking reaction. However, it is preferred that the cross-linking reaction takes place at approximately room temperature.

The product may be cross-linked either while still on its former or when removed therefrom.

This process may be used to cross-link polyurethane articles fabricated by means other than electrostatic spinning.

In a preferred embodiment, the spun product comprises fibers of a polyether polyurethane urea and the cross-linking agent used in a vapourisable haloalkylisocyanate such as chloromathylisocyanate. It is believed that the polyurethane chain of the polyurethane prosthesis contains some free amino acid groups which can be alkylated by the chlorine moiety to form a NH—$CH_2$ linkage. The haloalkylisocyanate reacts with these amino groups to cross-link the polymer.

An electrostatically spun polyurethane may be cross-linked in liquid media under conditions producing little alteration of both the microscopic and macroscopic appearance of the product. This may be effected by swelling the product in a liquid having little or no effect on the polyurethane (e.g. n-hexane) containing an appropriate amount of chloromethyl isocyanate (e.g. 1 to 90% v/v). If a suitable amount (typically 10% v/v) of chloromethyl isocyanate in n-hexane is used the overall flexibility and porosity of the product remain substantially unaltered after cross-linking. This reaction is also appropriate for cross-linking polyurethane products fabricated by processes other than electrostatic spinning.

Illustrative and non-limiting Examples of processes according to the present invention which are used to form a product according to the present invention are given below. It should, however, be appreciated that the Examples given below describe the invention purely by way of illustration, and that modifications of detail can be made within the scope of the invention.

EXAMPLES

1. A polytetramethylene ether polyurethane urea resin (Biomer, suppled by Ethicon) was dissolved in dimethyl acetamide and was electrostatically spun according to the process described in GB-A-No. 2,120,946 or GB-A-No. 2,121,286 onto cylindrical formers to produce a number of tubular electrostatically spun fibrous products having a fiber on the average about one micrometer in diameter.

One such product was immersed in a bath of dimethyl acetamide and had completely dissolved within two hours of immersion.

A second such product was placed, on its former, in a sealable glass container which was then evacuated to remove gas from the container and the product. A quantity of chloromethylisocyanate was introduced into the evacuated container without it directly contacting the product. The product was retained in that container for 24 hours at a temperature of approximately 20° C., whereupon the container is returned to atmospheric pressure, excess liquid chloromethylisocyanate is removed and the product is washed in water to remove any unreacted cross-linking agent adsorbed on the fibers.

The microscopic and macroscopic appearance of the thus treated product was compared with that of a similar, untreated product, which were observed to be substantially the same. It was also observed that the flexibility and porosity of the treated product was substantially the same as those of the untreated product. However, the elongation, flexural and burst strength and the resistance to creep of the treated product were superior to those of the untreated product.

The treated product was then immersed in a bath of dimethyl acetamide. After 24 hours immersion very little, if any of the product had dissolved, indicating that the fibers had been highly cross-linked. This also shows that the cross-linked material could not have been used in an electrostatic spinning process.

Thus, the process of the present invention produces an electrostatically spun product having improved strength and creep resistance properties but in which its porosity, flexibility and handleability have not been substantially adversely affected.

2. Solutions of Biomer in N,N dimethylacetamide may be easily cross-linked by direct addition of chloromethyl isocyanate.

Typically 10 grams of a 15% w/w solution of Biomer in N,N dimethyl acetamide is gelled within seconds by direct addition of 0.5 ml neat chloromethyl isocyanate to ultimately yield a hard elastomeric network which is no longer soluble in any non-degrading liquid.

3. Films of poly(ether urethanes; Tecoflex (Thermedic) prepared by extrusion and Pellethane (Bayer) cast from N,N dimethyl acetamide solution (2% w/w) were cross-linked by immersion in a solution of chloromethyl isocyanate in hexane (10% v/v) for 24 hours. After washing and drying all films having received this treatment were found to swell but not dissolve in N,N dimethyl acetamide unlike all untreated samples. The mechanical properties of the cross-linked films were found to be markedly superior to those which were untreated.

We claim:

1. A process for producing a medical prosthesis, comprising forming the prosthesis from an uncross-linked polyurethane and then at least partially cross-linking the polyurethane with a cross-linking agent, by treating the prosthesis with a vaporizable halo alkyl isocyanate and reacting said isocyanate with said polyurethane by vaporizing the isocyanate at a temperature below that temperature at which the polyurethane in its uncross-linked form tends to degrade and soften.

2. The process of claim 1 wherein the medical prosthesis is formed by molding.

3. The process of claim 2, wherein the cross-linking agent is incorporated into and molded with the polyurethane.

4. The process of claim 1, wherein the medical prosthesis is formed by dip-casting.

5. The process of claim 1, wherein the medical prosthesis is formed by electrostatically spinning a melt or solution of the polyurethane material onto an appropriately shaped former.

6. The process of claim 1, wherein the prosthesis is treated with the vaporization halo-alkyl isocyanate by immersing the prosthesis in a liquid containing the halo-alkyl isocyanate.

7. The process of claim 6, wherein the liquid comprises only the cross-linking agent.

8. The process of claim 6, wherein the liquid comprises a solution of the cross-linking agent in a solvent which will not dissolve or react with the polyurethane.

9. The process of claim 1, wherein the prosthesis is treated with the vaporizable halo-alkyl isocyanate by exposing the prosthesis to a vapor containing the halo-alkyl isocyanate.

10. The process of claim 1 wherein the halo-alkyl isocyanate is chloromethyl isocyanate.

11. The process of claim 1, wherein the cross-linking reaction takes place at approximately room temperature.

12. The process of claim 1, wherein the prosthesis is washed in water or an aqueous solution after treatment with the cross-linking agent.

* * * * *